United States Patent [19]

Forsberg

[11] 4,200,544

[45] * Apr. 29, 1980

[54] MAGNESIUM-CONTAINING GREASES AND METHOD FOR THEIR PREPARATION

[75] Inventor: John W. Forsberg, Mentor-on-the-Lake, Ohio

[73] Assignee: The Lubrizol Corporation, Wickliffe, Ohio

[*] Notice: The portion of the term of this patent subsequent to Jun. 13, 1995, has been disclaimed.

[21] Appl. No.: 914,718

[22] Filed: Jun. 12, 1978

Related U.S. Application Data

[63] Continuation-in-part of Ser. No. 760,315, Jan. 18, 1977, Pat. No. 4,094,801, which is a continuation-in-part of Ser. No. 681,627, Apr. 29, 1976, abandoned.

[51] Int. Cl.$^2$ .................. C10M 5/22; C10M 5/16; C10M 7/38; C10M 7/22
[52] U.S. Cl. ................................ 252/33.2; 252/39; 252/40
[58] Field of Search .................. 252/33.2, 39, 40

[56] References Cited

U.S. PATENT DOCUMENTS 4,094,801   6/1978   Forsberg ................ 252/33.2

FOREIGN PATENT DOCUMENTS

| | | | |
|---|---|---|---|
| 670620 | 4/1952 | United Kingdom | 252/33.2 |
| 687490 | 2/1953 | United Kingdom | 252/33.2 |
| 789820 | 1/1958 | United Kingdom | 252/33 |
| 797409 | 7/1958 | United Kingdom | 252/33.2 |
| 806595 | 12/1958 | United Kingdom | 252/33.2 |
| 997335 | 7/1965 | United Kingdom | 252/33.2 |
| 1005957 | 9/1965 | United Kingdom | 252/33.2 |
| 1052380 | 12/1966 | United Kingdom | 252/33.2 |
| 1054280 | 1/1967 | United Kingdom | 252/33.2 |

*Primary Examiner*—Irving Vaughn
*Attorney, Agent, or Firm*—James W. Adams, Jr.; William H. Pittman

[57] ABSTRACT

Magnesium-containing greases, particularly useful for bearing lubrication in high-temperature environments, are prepared by heating a mixture of magnesium hydroxide, magnesium oxide, hydrated magnesium oxide or a magnesium alkoxide; a carboxylic acid, a mixture thereof with a sulfonic acid, or an ester or salt of the same; water; and a liquid solubilizing agent for the acid, ester or salt. The amount of magnesium is such as to provide a basic grease.

13 Claims, No Drawings

MAGNESIUM-CONTAINING GREASES AND METHOD FOR THEIR PREPARATION

This application is a continuation-in-part of copending application Ser. No. 760,315, filed Jan. 18, 1977, now U.S. Pat. No. 4,094,801, which in turn is a continuation-in-part of application Ser. No. 681,627, filed Apr. 29, 1976, now abandoned.

This invention relates to new magnesium-containing compositions of matter and methods for the preparation. More particularly, it relates to non-carbonated magnesium-containing greases which are prepared by heating, at a temperature above about 30° C., a mixture comprising:

(A) at least one of magnesium hydroxide, magnesium oxide, hydrated magnesium oxide or a magnesium alkoxide;
(B) an oleophilic organic reagent comprising at least one carboxylic acid, a mixture thereof with at least one sulfonic acid, or an ester or alkali metal or alkaline earth metal salt of the same;
(c) water; and
(D) at least one relatively non-volatile, substantially inert, normally liquid solubilizing agent for component B;

The ratio of equivalents of magnesium to component B, calculated as the free acid, being at least about 5:1, and the amount of water present being at least sufficient to hydrate a substantial proportion of component A calculated as magnesium oxide.

Several methods are known for the preparation of basic magnesium compounds for use in lubricants, greases and the like. For example, U.S. Pat. No. 3,865,737 describes the formation of a highly basic magnesium-containing liquid dispersion by mixing an oil-soluble dispersing agent, magnesium oxide, a volatile aliphatic hydrocarbon solvent, alcohol, water and ammonia or an ammonium compound, treating the mixture with carbon dioxide, adding a non-volatile diluent oil and removing volatiles. Similarly, U.S. Pat. No. 3,629,109 describes the carbonation of a mixture of an oil-soluble organic acid or salt thereof, magnesium oxide, a lower aliphatic alcohol, water and an organic liquid diluent. The products obtained by these methods may be characterized, for the most part, as basic, oleophilic magnesium carbonates since an essential step in their preparation is reaction with carbon dioxide.

In accordance with the present invention, it has been discovered that highly basic magnesium greases may be prepared without reaction with carbon dioxide or similar acidic gases. The products obtained in accordance with the present invention, which are hereinafter sometimes referred to merely as "magnesium greases," are useful for lubricating bearings and the like which operate under conditions of very high temperature.

A principal object of the present invention, therefore, is to provide new oleophilic magnesium-containing compositions and a method for their preparation.

A further object is to provide a method for producing magnesium greases which does not necessitate reaction with carbon dioxide or a similar acidic gas.

Other objects will in part be obvious and will in part appear hereinafter.

Component A used in the method of this invention is magnesium hydroxide, magnesium oxide, hydrated magnesium oxide, a magnesium alkoxide, or a mixture of these. Magnesium hydroxide and magnesium oxide are, of course, represented by the formulas $Mg(OH)_2$ and $MgO$, respectively. Magnesium oxide exists in an inactive "dead burned" and a hydratable "reactive" form and the latter is the one which is useful in this invention although mixtures of the "reactive" form with minor amounts of the "dead burned" form may also be used. "Hydrated magnesium oxide," for the purpose of this invention, is magnesium oxide which is associated with water in an amount less than that required for conversion to magnesium hydroxide; that is, the amount of water is less than one mole per mole of magnesium oxide. As so defined, "hydrated magnesium oxide" may actually be a mixture of various proportions of magnesium oxide and magnesium hydroxide and its exact chemical nature is not critical to this invention. Typically, the amount of water present in "hydrated magnesium oxide" is at least about 0.7 mole per mole of the oxide.

The magnesium alkoxides, especially the lower alkoxides (i.e., those in which the alkyl groups contain 7 carbon atoms or less), are equivalent to magnesium oxide and hydroxide for the purpose of this invention; they are hydrolyzed by water to magnesium hydroxide under the conditions described hereinafter.

The equivalent weight of component A is half its molecular weight, since magnesium is a divalent element.

Component B is an oleophilic reagent comprising certain types of organic acidic compounds or salts or esters thereof. The suitable acids for this purpose are the carboxylic and sulfonic acids, including many of those known to be susceptible to overbasing and especially many of those disclosed in a number of U.S. patents such as U.S. Pat. Nos. 2,616,904; 2,695,910; 3,312,618; 3,746,643; 3,764,533; and the aforementioned 3,629,109. Those patents are incorporated by reference herein for their disclosure of suitable acidic oleophilic reagents.

Component B may be at least one carboxylic acid. Suitable carboxylic acids include aliphatic, cycloaliphatic and aromatic mono- and polybasic carboxylic acids free from acetylenic unsaturation, including naphthenic acids, alkyl- or alkenyl-substituted cyclopentanoic acids, alkyl- or alkenyl-substituted cyclohexanoic acids, and alkyl- or alkenyl-substituted aromatic carboxylic acids. The aliphatic acids generally contain at least 8 and preferably at least 12 carbon atoms. The cycloaliphatic and aliphatic carboxylic acids can be saturated or unsaturated. Specific examples include 2-ethylhexanoic acid, hydroxystearic acid, linolenic acid, propylene tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentanecarboxylic acid, myristic acid, dilauryldecahydronaphthalenecarboxylic acid, stearyl-octahydroindenecarboxylic acid, palmitic acid, acids formed by oxidation of petrolatum or of hydrocarbon waxes, and commercially available mixtures of two or more carboxylic acids such as tall oil acids, rosin acids, and the like. The equivalent weight of any such acid is its molecular weight divided by the number of carboxyl groups present therein.

Component B may also be a mixture of one or more of the above-described carboxylic acids with at least one sulfonic acid. Suitable sulfonic acids include those represented by the formulas $R^1(SO_3H)_r$ and $(R^2)_xT(SO_3H)_y$. In these formulas, $R^1$ is an aliphatic or aliphatic-substituted cycloaliphatic hydrocarbon or essentially hydrocarbon radical free from acetylenic unsaturation and containing up to about 60 carbon atoms. When $R^1$ is aliphatic, it usually contains at least about 15–18 carbon atoms; when it is an aliphatic-substituted cycloaliphatic radical, the aliphatic substituents usually contain a total of at least about 12 carbon atoms. Examples of $R^1$ are alkyl, alkenyl and alkoxyalkyl radicals, and aliphatic-substituted cycloaliphatic radicals wherein the aliphatic substituents are alkyl, alkenyl, alkoxy, alkoxyalkyl, carboxyalkyl and the like. Generally, the cycloaliphatic nucleus is derived from a cycloalkane or a cycloalkene such as cyclopentane, cyclohexane, cyclohexene or cyclopentene. Specific examples of $R^1$ are cetylcyclohexyl, laurylcyclohexyl, cetyloxyethyl, octadecenyl, and radicals derived from petroleum, saturated and unsaturated paraffin wax, and olefin polymers including polymerized monoolefins and diolefins containing about 1–8 carbon atoms per olefinic monomer unit. $R^1$ can also contain other substituents such as phenyl, cycloalkyl, hydroxy, mercapto, halo, nitro, amino, nitroso, lower alkoxy, lower alkylmercapto carboxy, carbalkoxy, oxo or thio, or interrupting groups such as —NH—, —O— or —S—, as long as the essentially hydrocarbon character thereof is not destroyed.

$R^2$ is generally a hydrocarbon or essentially hydrocarbon radical free from acetylenic unsaturation and containing about 4–60 aliphatic carbon atoms, preferably an aliphatic hydrocarbon radical such as alkyl or alkenyl. It may also, however, contain substituents or interrupting groups such as those enumerated above provided the essentially hydrocarbon character thereof is retained. In general, the non-carbon atoms present in $R^1$ or $R^2$ do not account for more than 10% of the total weight thereof.

The radical T is a cyclic nucleus which may be derived from an aromatic hydrocarbon such as benzene, naphthalene, anthracene or biphenyl, or from a heterocyclic compound such as pyridine, indole or isoindole. Ordinarily, T is an aromatic hydrocarbon nucleus, especially a benzene or naphthalene nucleus.

The subscript x is at least 1 and is generally 1–3. The subscripts r and y have an average value from about 1 to about 4 per molecule and are generally also 1.

Illustrative sulfonic acids useful as part of component B are mahogany sulfonic acids, petrolatum sulfonic acids, mono- and polywax-substituted naphthalene sulfonic acids, cetylchlorobenzene sulfonic acids, cetylphenol sulfonic acids, cetylphenol disulfide sulfonic acids, cetoxycapryl benzene sulfonic acids, dicetyl thianthrene sulfonic acids, di-lauryl beta-naphthol sulfonic acids, dicapryl nitronaphthalene sulfonic acids, paraffin wax sulfonic acids, unsaturated paraffin wax sulfonic acids, hydroxy-substituted paraffin wax sulfonic acids, tetraisobutylene sulfonic acids, tetra-amylene sulfonic acids, chloro-substituted paraffin wax sulfonic acids, nitroso-substituted paraffin wax sulfonic acids, petroleum naphthene sulfonic acids, cetylcyclopentyl sulfonic acids, lauryl cyclohexyl sulfonic acids, mono- and polywax-substituted cyclohexyl sulfonic acids, post-dodecylbenzene sulfonic acids, "dimer alkylate" sulfonic acids, and the like. These sulfonic acids are well known in the art and require no further discussion herein.

For the purpose of this invention, the equivalent weight of a sulfonic acid is its molecular weight divided by the number of sulfonic acid groups present therein. Thus, for a monosulfonic acid the equivalent weight is equal to the molecular weight.

Also useful as component B are the alkali metal and alkaline earth metal salts (e.g., sodium, potassium, magnesium, calcium, strontium or barium salts, with magnesium salts being preferred) and esters of the acids previously described. The suitable esters include those with monohydric alcohols free from acetylenic unsaturation and having about 1–25 carbon atoms, including monohydric alcohols such as methanol, ethanol, the butanols, the hexanols, allyl alcohol, crotyl alcohol, stearyl alcohol and oleyl alcohol, and polyhydric alcohols such as ethylene glycol, diethylene glycol, propylene glycol, glycerol, sorbitol, sorbitan and similar carbohydrates and derivatives of carbohydrates. When an ester is used as component B, it is converted to the magnesium salt of the free acid during the reaction with component A and water. In other words, the acidic portion of the ester is the operative portion for the purpose of this invention and the identity of the alcoholic portion thereof is immaterial. Thus, it will be appreciated that the equivalent weight of the ester for the purpose of this invention is its molecular weight divided by the number of groups present therein which are convertible by hydrolysis to carboxylate or sulfonate groups under the reaction conditions of the invention. If any of the ester groups remain unconverted, the ester is considered as inert to that extent for the purpose of calculating its equivalent weight.

Preferably, component B comprises a mixture of carboxylic and sulfonic acids (or salts or esters thereof) in which the weight ratio of carboxylic to sulfonic compounds is between about 4.5 and about 7.0. The equivalent weights of the acids are most often between about 300 and about 500. A particular preference is expressed for mixtures in which the sulfonic acids are alkylaromatic sulfonic acids, especially alkylbenzenesulfonic acids. Still more particularly preferred are mixtures of such sulfonic acids with fatty acids (which may be hydrogenated) and with carboxylic acids formed by oxidation of hydrocarbons such as petrolatum.

One of the characteristics of component B is that it is oleophilic. This means that it is soluble or at least stably dispersible (as defined hereinafter) in oil or similar non-polar organic liquids such as hexane, naphtha, Stoddard solvent, benzene, toluene and the like. While component B need not be oil-soluble, the oil-soluble sulfonic and carboxylic acids are preferred for the purposes of this invention. These oil-soluble compounds constitute a known subgenus of the previously described compounds useful as component B.

Component C is water, which may be used as a liquid or in the vapor phase (i.e., as steam). For the purpose of the present invention, the equivalent weight of water is considered to be 9 (half its molecular weight).

Component D is at least one relatively non-volatile, substantially inert, normally liquid solubilizing agent for component B. It need not be a solvent for component B in the sense that component B is entirely soluble therein when in the liquid state, but should be at least a partial solvent in the sense that relatively small proportions of component B, at least, when blended with component D in the liquid state will form a homogeneous mixture.

The term "relatively non-volatile" as used herein means a substance that does not evaporate in substantial quantities at atmospheric pressure and temperatures up to about 100° C. The term "substantially inert" is intended to mean that the liquid is inert to chemical or physical change under the conditions in which it is used so as not to materially interfere in an adverse manner with the preparation, storage, blending and/or functioning of the magnesium grease in the context of its intended use. For example, small amounts of a liquid can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Relatively non-volatile" and "substantially inert" as used herein are thus readily understood and appreciated by those of ordinary skill in the art.

Among the preferred solubilizing agents are non-polar compounds or mixtures of compounds such as mineral oil, bright stock, and alkylbenzenes of the type present as unsulfonated residue in alkylbenzenesulfonic acids. The latter will usually be present in at least minor quantities. Also suitable are somewhat more polar liquids such as ethylene glycol, propylene glycol, ethylene glycol monomethyl ether, ethylene glycol monobutyl ether, ethylene glycol dimethyl ether, diethylene glycol and its ethers, and wax-derived alcohol mixtures. It is also within the scope of the invention to use mixtures of two or more of these materials.

As previously noted, the ratio of equivalents of magnesium to the acid portion of component B is at least about 5:1 and usually up to about 20:1. This ratio is hereinafter sometimes referred to as the "magnesium ratio." (It will be appreciated that the magnesium ratio is such as to produce a basic magnesium grease.) If component B is the free acid or an ester thereof or salt of a metal other than magnesium, the ratio of component A to component B will be identical to the magnesium ratio. If component B is a magnesium salt of one of the above, the ratio of component A to component B will be somewhat less than the magnesium ratio since part of the magnesium is provided by component B.

The molar ratio of water (component C) to component A (hereinafter sometimes designated the "water ratio") is also critical. It should be at least sufficient to hydrate a substantial proportion of component A, calculated as magnesium oxide. If component A is magnesium hydroxide, it already contains at least this amount of water and the amount of additional water will depend on the nature of the product desired and the intended use thereof. On the other hand, if component A is anhydrous magnesium oxide the water ratio should generally be at least about 0.7:1 so as to produce the hydrated magnesium oxide referred to hereinabove. Most often, a water ratio between about 0.7:1 and about 3.0:1 is adequate to produce a grease of this invention.

The ratio of component D to component A may be varied so as to provide a composition having the desired grease consistency. For high temperature lubrication applications such as the ones for which the greases of this invention are particularly suitable, a weight ratio between about 1.5:1 and about 5.0:1, and usually between about 2:1 and about 4:1, is particularly suitable.

The magnesium greases of this invention are prepared by merely blending the components described hereinabove and heating the resulting blend to a temperature above about 30° C., preferably from about 30° to about 125° C. and most often from about 40° to about 100° C. Reproducibility of the properties of the magnesium greases is frequently enhanced by incorporating in the reaction mixture a lower alkanol such as ethanol, 1-propanol, 2-propanol, 1-butanol or the like, usually in an amount from about 30% to about 50% by weight of the water present.

The water and lower alkanol (if present) should remain in the reaction mixture during the preparation of the grease, but should be removed prior to its use. This may be conveniently done by methods known in the art, such as by stripping (typically in an inert atmosphere such as nitrogen) at temperatures between about 150° and about 200° C.

In order of addition of the various components during the preparation of the magnesium grease is not critical. For the purposes of this invention, it is often convenient to first combine A, B and D and subsequently to add component C and any lower alkanol used either all at once or incrementally. Additional component D may be added after the preparation of the grease as necessary to provide the desired consistency.

The molecular structures of the compositions comprising the magnesium greases of this invention are not known and are not a critical aspect of the invention. The greases are, in general, most conveniently defined in terms of the method for their preparation.

Copending, allowed application Ser. No. 760,315, filed Jan. 18, 1977, is incorporated by reference herein for its disclosure of magnesium complexes of which the magnesium greases of this invention are a subgenus. Examples 1-16 in that application are illustrative of suitable methods of preparing such complexes, and those skilled in the art will readily be able to modify the procedures described in said working examples as necessary in order to produce magnesium greases of this invention. The preparation of such greases is also illustrated by the following examples in which all parts are by weight.

EXAMPLE 1

A mixture of 1525 parts of bright stock, 900 parts of magnesium oxide, 480 parts of "Hydrex 440" (a mixture of hydrogenated fatty acids obtainable from Union Camp Corporation) and 84 parts of an alkylbenzenesulfonic acid having an equivalent weight of about 430 and containing about 22% unsulfonated alkylbenzene is heated to 93° C. and 450 parts of water is added over 5 hours at 93°-96° C. An additional 140 parts of bright stock is added at 93° C. and the temperature is raised to 170°-175° C. as the mixture is blown with nitrogen to remove volatiles including water. It is then cooled to 120° C. and an additional 300 parts of bright stock is added. Upon cooling to room temperature, the desired magnesium grease is obtained.

EXAMPLE 2

A mixture of 16 parts of the alkylbenzenesulfonic acid of Example 1, 305 parts of bright stock, 180 parts of magnesium oxide and 96 parts of "Hydrex 440" is heated to 95° C. and blown with steam for 2 hours. The temperature is increased to 145°-150° C., an additional 28 parts of bright stock is added and the mixture is blown with air as the temperature is increased to 170° C. over 15 minutes. The mixture is then cooled to room temperature and an additional 44 parts of bright stock is added to yield the desired magnesium grease.

EXAMPLE 3

A mixture of 1875 parts of 200 neutral mineral oil, 760 parts of magnesium oxide, 405 parts of "Hydrex 440" and 71 parts of the alkylbenzenesulfonic acid of Example 1 is heated to 71° C., with stirring. It is then heated to 82°–87° C. and 130 parts of 1-propanol is added, followed by dropwise addition of 320 parts of water over 3 hours. Also added is 94 parts of a hydrogenated styrene-butadiene polymer which improves resistance to water of the product grease.

The mixture is stripped of volatiles by blowing with nitrogen at temperatures up to 165° C., and is then cooled to 110°–115° C. and charged with 35 parts of "Vanlube SL," an arylamine oxidation inhibitor supplied by R. T. Vanderbilt Company, and 130 parts of an 87% solution in mineral oil of a zinc di-(lower alkyl)-phosphorodithioate, added to improve the extreme pressure properties of the grease. Finally, the mixture is cooled to room temperature and an additional 800 parts of 200 neutral mineral oil is added to reduce it to the desired consistency.

EXAMPLE 4

The procedure of Example 3 is repeated, except that the sulfonic acid is replaced by an equal number of equivalents of "Hydrex 440." A similar grease is obtained.

EXAMPLE 5

The procedure of Example 3 is repeated except that the alkylbenzenesulfonic acid is replaced by an equal number of equivalents of one having an equivalent weight of about 385 and containing about 24% unsulfonated alkylbenzene. A similar grease is obtained.

The greases of this invention may be used in conventional manner for lubrication of bearings and the like. They are particularly useful in applications where extremely high temperatures are encountered, such as for lubrication of bearings in hot rolling mills for the production of steel. Especially useful for this purpose are greases of the type represented by Example 3, which, in addition to being useful at high temperatures, have relatively low viscosity at extremely low temperatures (e.g., around 0° C.) which makes them suitable for transmission (e.g., by pumping) in unheated environments such as are sometimes encountered in various portions of steel mills.

What is claimed is:

1. A method for preparing a non-carbonated magnesium-containing grease which comprises heating, at a temperature above about 30° C., a mixture comprising:
   (A) at least one of magnesium hydroxide, magnesium oxide, hydrated magnesium oxide, or a magnesium alkoxide;
   (B) an oleophilic organic reagent comprising at least one carboxylic acid, a mixture thereof with at least one sulfonic acid, or an ester or alkali metal or alkaline earth metal salt of the same;
   (C) water; and
   (D) at least one relatively non-volatile, substantially inert, normally liquid solubilizing agent for component B;
   the ratio of equivalents of magnesium to component B, calculated as the free acid, being at least about 5:1, and the amount of water present being at least sufficient to hydrate a substantial proportion of component A calculated as magnesium oxide.

2. A method according to claim 1 wherein component B is a mixture of sulfonic and carboxylic acids or salts thereof.

3. A method according to claim 2 wherein the molar ratio of component C to component A is at least about 0.7:1.

4. A method according to claim 3 wherein component A is magnesium oxide.

5. A method according to claim 2 wherein component B is a mixture of at least one alkylaromatic sulfonic acid and at least one hydrogenated fatty acid or carboxylic acid formed by oxidation of petrolatum.

6. A method according to claim 5 wherein the sulfonic acid is at least one alkylbenzenesulfonic acid.

7. A method according to claim 6 wherein the mole ratio of component C to component A is at least about 0.7:1.

8. A method according to claim 7 wherein component A is magnesium oxide.

9. A method according to any of claims 1–8 wherein the mixture also contains at least one lower alkanol.

10. A method for preparing a non-carbonated magnesium-containing grease which comprises heating, at a temperature from about 40° to about 100° C., a mixture comprising:
    (A) magnesium oxide;
    (B) a mixture of hydrogenated fatty acids and alkylbenzenesulfonic acids having an equivalent weight from about 300 to about 500, the weight ratio of fatty acids to sulfonic acids being between about 4.5 and about 7.0;
    (C) water; and
    (D) at least one of mineral oil, bright stock and the alkylbenzene whose sulfonation product is component B;
    the ratio of equivalents of component A to component B being at least about 5:1 and the molar ratio of component C to component A being between about 0.7:1 and 3.0:1.

11. A method according to claim 10 wherein the mixture also contains at least one lower alkanol in the amount of about 30% to about 50% by weight of component C.

12. A method according to claim 11 wherein the lower alkanol is 1-propanol.

13. A grease prepared by the method of claim 1, 2, 4, 5, 6, 8, or 10.

* * * * *